United States Patent
Carrascal et al.

(10) Patent No.: US 7,135,045 B2
(45) Date of Patent: Nov. 14, 2006

(54) COMPOSITION FOR DYEING HUMAN HAIR

(75) Inventors: Isabel Vega Carrascal, Valladolid (ES); Bernd Nöcker, Ober Ramstadt (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 317 days.

(21) Appl. No.: 10/791,920

(22) Filed: Mar. 2, 2004
(Under 37 CFR 1.47)

(65) Prior Publication Data
US 2004/0231069 A1   Nov. 25, 2004

(30) Foreign Application Priority Data

| Mar. 6, 2003 | (EP) | ................................ 03 004 864 |
| Mar. 6, 2003 | (EP) | ................................ 03 004 865 |
| Mar. 6, 2003 | (EP) | ................................ 03 004 866 |

(51) Int. Cl.
*A61K 7/13*   (2006.01)

(52) U.S. Cl. ...................... 8/405; 8/426; 8/435; 8/455; 8/463; 8/585

(58) Field of Classification Search ................. 8/405, 8/426, 435, 455, 463, 585
See application file for complete search history.

(56) References Cited

U.S. PATENT DOCUMENTS

| 2,501,184 A | 3/1950 | Michaels et al. ................. 8/10 |
| 4,182,612 A * | 1/1980 | Sokol et al. .................... 8/426 |
| 5,601,620 A | 2/1997 | Ishikawa ....................... 8/405 |

FOREIGN PATENT DOCUMENTS

| EP | 1 022 014 A1 | 7/2000 |
| FR | 762 985 A | 4/1934 |

OTHER PUBLICATIONS

D.F. Williams: "Chemistry and Technology of the Cosmetics and Toiletries Industry", 1992, Blackie Academic & Professional, Xp002251416, pp. 92-93.

* cited by examiner

*Primary Examiner*—Eisa Elhilo
(74) *Attorney, Agent, or Firm*—Norris McLaughlin & Marcus PA

(57) ABSTRACT

This invention relates to a hair dyeing composition showing excellent dyeing ability comprising at least one direct acting hair dye and benzylurea and/or benzyl carbamate and/or N-(2-methoxybenzyl) urea. The direct acting hair dyes are preferably selected from anionic, acidic dyestuffs. In addition to benzylurea and/or benzyl carbamate and/or N-(2-methoxybenzyl) urea compositions further comprise organic solvents as penetration enhancers. Compositions according to the invention has a pH in the range from 1 to 5 and preferably comprises polymeric thickening agents, organic and/or inorganic acids and conditioning agents.

19 Claims, No Drawings

COMPOSITION FOR DYEING HUMAN HAIR

This invention relates to a hair dyeing composition showing excellent dyeing ability comprising at least one direct acting hair dye and benzylurea and/or benzyl carbamate and/or N-(2-methoxybenzyl) urea. It should be well understood that the colouring composition of this invention are ready to use composition and therefore do not require any mixing with additional agents such as oxidizers prior to application.

Hair colouring is a common practice for ages. Oxidative colouration has been widely used for achieving durable, brilliant hair colour. Direct dyes, mainly of cationic character, have also found their applications for colouring hair. The colours so achieved are brilliant but often lacking durability. Recently, anionic direct dyes have been found to be very powerful for changing hair colour permanently and to achieve long lasting, brilliant colours. The colouring agents with anionic dyes are so formulated that the optimum conditions are realised for achieving the highest dyestuff penetration into hair. European patent application with laid open number EP 1022014 describes such compositions comprising anionic dyestuffs, solvents, as aid to enhance penetration of said dyestuffs, and a buffer solution to adjust the pH of the dyeing agent in the range from 2 to 6. For enhancing penetration of dyestuffs, solvents are used such as ethanol, benzyl alcohol, propylene carbonate, dipropylene glycol. Products are found on the professional hair dressing market applying this technology.

U.S. Pat. No. 5,601,620, as well, discloses hair colouring agents with acid dyes, an organic solvent and at least one polysiloxane as a conditioner. The dyeing compositions disclosed here are having a pH in the range of 1.5–4.5. In this patent again ethanol, benzyl alcohol and dipropylen glycol are mentioned to be the penetration enhancers preferred.

In practice further need of higher dyeing ability is obviously desired by professional hair dressing practitioners and also end consumers in order to achieve more brilliant and long lasting (fastness against washing) colorations.

Recently, it has surprisingly been found out that hair colouring compositions on aqueous basis and direct acting dyes comprising, in addition to the conventional penetration enhancers, benzylurea and/or benzyl carbamate and/or N-(2-methoxy-benzyl) urea showing higher colouring ability than that of comprising only conventional solvents as penetration enhancers. Although the underlying mechanism of such effect is not very well understood, speculatively it may be observed because of synergistic interaction of benzylurea, benzyl carbamate or N-(2-methoxybenzyl) urea and the penetration enhancer contained in the colouring compositions. This invention is explicitly suitable for colouring hair with direct acting dyestuffs and therefore, the compositions are free from any oxidation dye precursors and/or coupling agents.

Colouring compositions according to the invention comprises benzylurea and/or benzyl carbamate and/or N-(2-methoxybenzyl) urea and at least one direct acting hair dye preferably of acidic, anionic character.

Concentration of benzyl urea and/or benzyl carbamate and/or N-(2-methoxybenzyl) urea in the colouring compositions of the present invention should be between 0.1–10%, preferably 0.1–7%, more preferably 0.2–5% and most preferably 0.2–3% by weight, calculated to the total composition.

According to the invention the suitable direct acting dyes are acidic, anionic dyes. Those are customarily incorporated in an amount from about 0.001% to about 5%, preferably about 0.01% to about 2.5%, in particular about 0.05% to about 2.5% by weight, calculated to the total composition, into the colouring compositions.

Examples for suitable anionic dyestuffs are:

| | |
|---|---|
| Acid Black 1, | C.I.-No. 20,470; |
| Acid Blue 1, | C.I.-No. 42,045; |
| Food Blue 5, | C.I.-No. 42,051; |
| Acid Blue 9, | C.I.-No. 42,090; |
| Acid Blue 74, | C.I.-No. 73,015; |
| Acid Red 18, | C.I.-No. 16,255; |
| Acid Red 27, | C.I.-No. 16,185; |
| Acid Red 87, | C.I.-No. 45,380; |
| Acid Red 92, | C.I.-No. 45,410; |
| Acid Orange 7, | C.I.-No. 15,510; |
| Acid Violet 43, | C.I.-No. 60,730; |
| Acid Yellow 1, | C.I.-No. 10,316; |
| Acid Yellow 23, | C.I.-No. 19,140; |
| Acid Yellow 3, | C.I.-No. 47,005; |
| Food Yellow No. 8, | C.I.-No. 14,270; |
| D&C Brown No. 1, | C.I.-No. 20,170; |
| D&C Green No. 5, | C.I.-No. 61,570; |
| D&C Orange No. 4, | C.I.-No. 15,510; |
| D&C Orange No. 10, | C.I.-No 45,425:1; |
| D&C Orange No. 11, | C.I.-No. 45,425; |
| D&C Red No. 21, | C.I.-No. 45,380:2; |
| D&C Red No. 27, | C.I.-No. 45,410:1; |
| D&C Red No. 33, | C.I.-No. 17,200; |
| D&C Yellow No. 7, | C.I.-No. 45,350:1; |
| D&C Yellow No. 8, | C.I.-No. 45,350; |
| FD&C Red No. 4, | C.I.-No. 14,700; |
| FD&C Yellow No. 6, | C.I.-No. 15,985. |

Direct acting cationic dyes can also be incorporated into the colouring compositions at a concentration less than 0.5%, preferably less than 0.25% by weight calculated to the total concentration of the composition. It should be kept in mind that those are less suited for the colouring compositions described here. Examples to those cationic dyes are:

| | |
|---|---|
| Basic Blue 6, | C.I.-No. 51,175; |
| Basic Blue 7, | C.I.-No. 42,595; |
| Basic Blue 9, | C.I.-No. 52,015; |
| Basic Blue 26, | C.I.-No. 44,045; |
| Basic Blue 41, | C.I.-No. 11,154; |
| Basic Blue 99, | C.I.-No. 56,059; |
| Basic Brown 4, | C.I.-No. 21,010; |
| Basic Brown 16, | C.I.-No. 12,250; |
| Basic Brown 17, | C.I.-No. 12,251; |
| Natural Brown 7, | C.I.-No. 75,500; |
| Basic Green 1, | C.I.-No. 42,040; |
| Basic Red 2, | C.I.-No. 50,240; |
| Basic Red 12 | C.I.-No. 48,070; |
| Basic Red 22, | C.I.-No. 11,055; |
| Basic Red 76, | C.I.-No. 12,245; |
| Basic Violet 1, | C.I.-No. 42,535; |
| Basic Violet 3, | C.I.-No. 42,555; |
| Basic Violet 10, | C.I.-No. 45,170; |
| Basic Violet 14, | C.I.-No. 42,510; |
| Basic Yellow 57. | C.I.-No. 12,719. |

Plant dyestuffs can also be used alone or in combination with synthetic direct-acting dyestuffs, for example henna (red or black), alkanna root, laccaic acid, indigo, logwood powder, madder root and rhubarb powder, etc.

It is self understood that the compositions according to the present invention comprise organic solvents as a penetration enhancers and also as a solubilzers for especially direct acting dyes. Examples of such "penetration enhancers" are benzyloxy ethanol, benzyl alcohol, phenoxy ethanol, phenoxy isopropanol, methyl phenoxy ethanol, benzyl glycerol, N-benzyl formide, N-methyl pyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 1% to 50%, preferably 1–40%, more preferably 1–30% and most preferably 1–25% by weight calculated to the total composition.

The pH of such compositions is in the range of 1.0–5.0, preferably 1.5 to 4.5, more preferably 2 to 4 and most preferably 2–3.5. The pH of the compositions is adjusted to the desired value with an organic and/or inorganic or their mixtures. Suitable organic acids are such as citric acid, lactic acid, tartaric acid, malic acid, maleic acid, fumaric acid, levulinic acid, butyric acid and hydroxy butyric acids, valeric acid, oxalic acid, succinic acid, mandelic acid, glycolic acid, glucuronic acid, propionic acid, salicylic acid or acetic acid and inorganic acids are such as hydrochloric acid, phosphoric acid, sulphuric acid, nitric acid. Concentration of the organic and/or inorganic acids or their mixtures should be adjusted in a way that colouring composition so obtained has a pH value between 1.0–5.0, preferably 1.5 to 4.5, more preferably 2 to 4 and most preferably 2–3.5. Typically concentration for acids can be 0.2–30% by weight, preferably 0.5–15% by weight, more preferably 0.5–8% by weight and most preferably 0.5–6% by weight. The pH of the colouring composition can also be adjusted to the required pH by using alkaline solution such as sodium hydroxide, potassium hydroxide or their salts with those acids mentioned above in the case that at the selected acid concentration pH of the composition is lower than that of the aimed value.

The hair dyeing compositions according to the invention preferably also contain thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof, synthetic polymers such as the various polyacrylic acids, etc., in amounts from about 0.3% to about 5% by weight, calculated to the total composition and depending on the desired consistency thereof.

Optionally, the colouring composition of this invention comprises hair conditioning agents. Conditioning agents can be selected from oily substances, non-ionic substances, cationic amphiphilic ingredients, cationic polymers or their mixtures. Oily substances are selected from such as silicone oils either volatile or non-volatile, natural and synthetic oils. Among silicone oils those can be added to the pre-treatment composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myri-state palmitate, stearate and isostearate, oleyl oleate, isocetyl stearate, hexyl laurate, dibutyl adipate, dioctyl adipate, myristyl myristate and oleyl erucate.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula I or II, respectively,

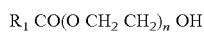 formula I

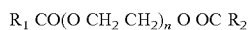 formula II where $R_1$ and $R_2$ are independent from each other saturated, unsaturated or branched or non-branched alkyl chain with 7 to 21 C atoms and n is typically 2–100.

Colouring composition can contain cationic amphiphilic conditioning ingredients according to the formula III, but not limited to.

Formula III

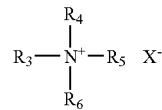

where $R_3$ is a saturated or unsaturated, branched or non-branched alkyl chain with 8–22 C atoms or

where $R_7$ is saturated or unsaturated, branched or non-branched alkyl chain with 7–21 C atoms and n has typical value of 1–4 or

where $R_8$ is saturated or unsaturated, branched or non-branched alkyl chain with 7–21 C atoms and n has typical value of 1–4, and $R_4$ is H or unsaturated or saturated, branched or non-branched alkyl chain with 1–22 C atoms or

or

where $R_7$, $R_8$ and n are same as above.

$R_5$ and $R_6$ are H or lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Colouring composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Typical concentration range for any of the conditioners mentioned above can be 0.01–5% by weight, preferably 0.03–2% by weight and more preferably 0.05–0.75% by weight.

The hair dyeing composition according to the invention can also comprise surface-active substances, although it does not constitute a tinting shampoo.

These can be non-ionic and/or amphoteric or zwitterionic.

Preferred are nonionic surfactants in an amount ranging between about 0.5% and about 5%, calculated to the total composition.

Suitable nonionic surfactants are compounds from the category of alkyl polyglucosides with the general formula

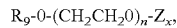

wherein $R_9$ is an alkyl group with 8 to 20, preferably 10 to 14 carbon atoms, $Z_x$ is a saccharide group with 5 to 6 carbon atoms, n stands for a number from 0 to 10, and x is a number between 1 and 5, preferably 1.1 to 2.5.

Further nonionic surfactants useful in the compositions according to invention are $C_{10}$–$C_{22}$-fatty alcohol ethoxylates.

Especially suited $C_{10}$–$C_{22}$-fatty alcohol ethers are the alkyl polyglycol ethers known by the generic terms "Laureth", "Myristeth", "Oleth", "Ceteth", "Deceth", "Stearet-h"and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Other additionally useful surfactants are, for example, the various sorbitan esters, such as polyethylene glycol sorbitan stearic acid ester, fatty acid polyglycol ester or also mixed condensates of ethylene oxide and propylene oxide, as they are on the market, for example, under the trade name "Pluronics$^R$".

Further additionally useful surfactants are amineoxides.

Such amineoxides are state of the art, for example $C_{12}$–$C_{18}$-alkyl dimethyl amineoxides such as lauryl dimethyl amineoxide, $C_{12}$–$C_{18}$-alkyl amidopropyl or ethyl amineoxides, $C_{12}$–$C_{18}$-alkyl di(hydroxyethyl) or (hydroxypropyl) amineoxides, or also amineoxides with ethylene oxide and/or propylene oxide groups in the alkyl chain.

Suitable amineoxides are on the market, for example, under the trade names "Ammonyx®", "Aromox®"or "Genaminox®".

Further optional surfactant components are fatty acid mono- and dialkanolamides, such as coco fatty acid monoethanolamide and myristic fatty acid monoisopropanolamide.

Suitable amphoteric or zwitterionic surfactants are in particular the various known betaines such as fatty acid amidoalkyl betaines and sulfobetaines; for example lauryl hydroxy sulfobetaine; long-chain alkyl amino acids, such as cocoaminoacetate, cocoaminopropionate and sodium cocoamphopropionate and -acetate have also proven suitable.

In detail it is possible to use betaines of the structure

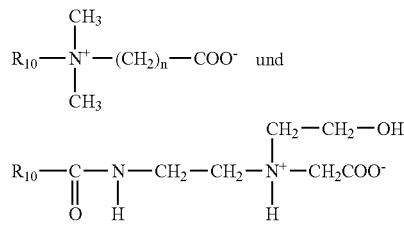

wherein $R_{10}$ is a $C_8$–$C_{18}$-alkyl group and n is 1 to 3, sulfobetaines of the structure

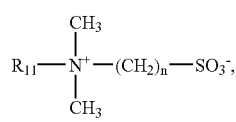

wherein $R_{11}$ is a $C_8$–$C_{18}$-alkyl group and n is 1 to 3, and amidoalkyl betaines of the structure

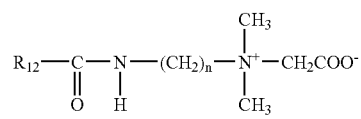

wherein $R_{12}$ is a $C_8$–$C_{18}$-alkyl group and n is 1 to 3,

Preferred are fatty acid amidoalkyl betaines, in particular cocoamidopropyl betaine, and cocoamphoacetate and -propionate, in particular the sodium salts thereof.

Colouring compositions of the present invention can be in the form of gel or emulsion. In the case of gel type of preparations the colouring compositions contain polymeric thickeners as mentioned above. In the case that colouring compositions are in emulsion form, the compositions may then contain fatty alcohols with 12 to 22 carbon atoms and non-ionic emulsifier such as ethoxylated fatty alcohols with general formula (IV)

$$R_{13}(O\ CH_2\ CH_2)_n OH \qquad \text{formula IV}$$

where $R_{13}$ is saturated or unsaturated, branched or non-branched alkyl chain with 8–22 C atoms and n has typical value of 2–100.

The viscosity of the compositions according to the invention preferably ranges from about 1,000 to about 60,000, in particular about 2,000 to 50,000, especially about 5,000 to 40,000 mPa.s, measured at 20° C. with a Brookfield rotation viscosimeter, with spindle 5 at 5 rpm.

The invention is illustrated with the following examples but not limited to.

EXAMPLE 1

|  | A | B |
| --- | --- | --- |
| Acid red 33 | 0.5 | 0.5 |
| Ethanol | 15.00 | 15.00 |
| Benyzlurea | 1.70 | — |
| PVM/MA Decadine Crosspolymer | 2.50 | 2.50 |
| Sodium hydroxide | 0.25 | 0.25 |
| Lactic acid | 4.50 | 4.50 |
| Dimethicone copolyol | 1.00 | 1.00 |
| Water | to 100 | to 100 |
| pH | 3.0 | 3.0 |

The viscosity of the compositions is 30,000 mPa.s measured at 20° C. with a Brookfield rotation viscosimeter, with spindle 5 at 5 rpm.

An intensive magenta colour is achieved on goat tress with composition A. With composition B the colour is less intensive

EXAMPLE 2

|  | A | B |
| --- | --- | --- |
| Acid violet 43 | 0.3 | 0.3 |
| Ethanol | 15.00 | 15.00 |

-continued

|  | A | B |
|---|---|---|
| Benyzlurea | 1.70 | — |
| PVM/MA Decadine Crosspolymer | 2.50 | 2.50 |
| Sodium hydroxide | 0.25 | 0.25 |
| Lactic acid | 4.50 | 4.50 |
| Dimethicone copolyol | 1.00 | 1.00 |
| Water | to 100 | to 100 |
| pH | 3.0 | 3.0 |

The viscosity of the compositions is 30,000 mPa.s measured at 20° C. with a Brookfield rotation viscosimeter, with spindle 5 at 5 rpm.

A dark violet colour is achieved on goat tress with composition A. With composition B the colour is less intensive For both examples 1 and 2, preparations A are examples to illustrate the invention. Preparations B are comparative preparations and not illustrating the invention The colouring compositions in examples 1 and 2 are prepared by dissolving firstly benzylurea, if present, in ethanol-water mixture at around 55° C. Into the solution, polymer and the remaining raw materials are added and mixed until homogeneity.

Colouring test is carried out with both preparations using a goat hair tress. Amount of colouring composition applied is approximately 1 g/g goat hair and coloruing is achieved by processing at 50° C. for 20 min. Afterwards the tresses are rinsed with water and shampooed once. After air drying, colour measurements are carried out with a commercial equipment (Minolta CR-200) in order to determine the difference in colour nature and intensity. Delta E values are calculated from the L, a and b values measured before and after colouration. Results are presented in Table I.

TABLE I

|  |  | Delta E |
|---|---|---|
| Example 1 | A (invention) | 70.3 |
|  | B (non-inventive) | 52.7 |
| Example 2 | A (invention) | 64.2 |
|  | B (non-inventive) | 44.7 |

It should be noted that the higher the delta E value the stronger the difference. It is very obvious from the results presented in Table I that the compositions comprising benzylurea (compositions A) are showing higher colouring ability than those of without (compositions B).

Similar results are obtained with the examples below. Examples 3 to 5 are prepared in the same way as described for Examples 1 and 2 above.

EXAMPLE 3

| Acid Violet 43 | 0.30 |
|---|---|
| Acid black 1 | 0.30 |
| DC Orange 4 | 0.20 |
| Acid red 33 | 0.20 |
| Ethanol | 15.00 |
| Benzylurea | 1.70 |
| PVM/MA Decadine | 2.50 |
| Crosspolymer |  |
| Sodium hydroxide | 0.25 |
| Lactic acid | 4.50 |

-continued

| Dimethicone copolyol | 1.00 |
|---|---|
| Water | to 100 |
| pH | 3.0 |

The viscosity of the compositions is 28,500 mPa.s measured at 20° C. with a Brookfield rotation viscosimeter, with spindle 5 at 5 rpm.

An intensive blue-black colour is achieved on goat tress. Exclusion of benzylurea results in a less intensive colouration.

EXAMPLE 4

| Acid Violet 43 | 0.30 |
|---|---|
| Acid black 1 | 0.30 |
| DC Orange 4 | 0.20 |
| Acid red 33 | 0.20 |
| Benzyloxyethanol | 1.00 |
| Ethanol | 10.00 |
| Benzylurea | 1.70 |
| Hydroxyethylcellulose | 1.50 |
| Sodium hydroxide | 0.25 |
| Phosphoric acid to pH 2.5 | q.s. |
| Dimethicone copolyol | 1.00 |
| Water | to 100 |

The viscosity of the compositions is 20,000 mPa.s measured at 20° C. with a Brookfield rotation viscosimeter, with spindle 5 at 5 rpm.

An intensive blue-black colour is achieved on goat tress. Exclusion of benzylurea results in a less intensive colouration.

EXAMPLE 5

| Acid red 52 | 0.50 |
|---|---|
| DC Orange 4 | 0.25 |
| Benzyloxyethanol | 1.00 |
| Ethanol | 10.00 |
| Benzylurea | 1.70 |
| Hydroxyethylcellulose | 1.50 |
| Sodium hydroxide | 0.25 |
| Lactic acid | 4.00 |
| Phosphoric acid to pH 2.0 | q.s. |
| Dimethicone copolyol | 1.00 |
| Water | to 100 |

The viscosity of the compositions is 18,800 mPa.s measured at 20° C. with a Brookfield rotation viscosimeter, with spindle 5 at 5 rpm.

An intensive red colour is achieved on goat tress. Exclusion of benzylurea results in a less intensive colouration.

EXAMPLE 6

|  | A | B |
|---|---|---|
| Acid red 33 | 0.5 | 0.5 |
| Ethanol | 15.00 | 15.00 |
| Benzyl carbamate | 1.70 | — |
| PVM/MA Decadine | 2.50 | 2.50 |

-continued

|  | A | B |
|---|---|---|
| Crosspolymer |  |  |
| Sodium hydroxide | 0.25 | 0.25 |
| Lactic acid | 4.50 | 4.50 |
| Dimethicone copolyol | 1.00 | 1.00 |
| Water | to 100 | to 100 |
| pH | 3.0 | 3.0 |

The viscosity of the compositions is 30,000 mPa.s measured at 20° C. with a Brookfield rotation viscosimeter, with spindle 5 at 5 rpm.

An intensive magenta colour is achieved on goat tress with composition A. With composition B the colour is less intensive

EXAMPLE 7

|  | A | B |
|---|---|---|
| Acid violet 43 | 0.3 | 0.3 |
| Ethanol | 15.00 | 15.00 |
| Benyzl carbamate | 1.70 | — |
| PVM/MA Decadine Crosspolymer | 2.50 | 2.50 |
| Sodium hydroxide | 0.25 | 0.25 |
| Lactic acid | 4.50 | 4.50 |
| Dimethicone copolyol | 1.00 | 1.00 |
| Water | to 100 | to 100 |
| pH | 3.0 | 3.0 |

The viscosity of the compositions is 30,000 mpa.s measured at 20° C. with a Brookfield rotation viscosimeter, with spindle 5 at 5 rpm.

A dark violet colour is achieved on goat tress with composition A. With composition B the colour is less intensive For both examples 6 and 7, preparations A are examples to illustrate the invention. Preparations B are comparative preparations and not illustrating the invention The compositions are prepared as given under Examples 1 and 2. Colouring comparison is as well carried out in the same way as in Examples 1 and 2. The results are presented in Table II.

TABLE II

|  |  | Delta E |
|---|---|---|
| Example 6 | A (invention) | 70.3 |
|  | B (non-inventive) | 52.7 |
| Example 7 | A (invention) | 64.2 |
|  | B (non-inventive) | 44.7 |

It is very obvious from the results presented in Table II that the compositions comprising benzyl carbamate (compositions A) are showing higher colouring ability than those of without (compositions B).

Similar results are obtained with the examples below. Examples 8 to 10 are prepared in the same way as described for Examples 1 and 2 above.

EXAMPLE 8

| Acid Violet 43 | 0.30 |
|---|---|
| Acid black 1 | 0.30 |
| DC Orange 4 | 0.20 |
| Acid red 33 | 0.20 |
| Ethanol | 15.00 |
| Benzyl carbamate | 1.70 |
| PVM/MA Decadine Crosspolymer | 2.50 |
| Sodium hydroxide | 0.25 |
| Lactic acid | 4.50 |
| Dimethicone copolyol | 1.00 |
| Water | to 100 |
| pH | 3.0 |

The viscosity of the compositions is 28,500 mPa.s measured at 20° C. with a Brookfield rotation viscosimeter, with spindle 5 at 5 rpm.

An intensive blue-black colour is achieved on goat tress. Exclusion of benzyl carbamate results in a less intensive colouration.

EXAMPLE 9

| Acid Violet 43 | 0.30 |
|---|---|
| Acid black 1 | 0.30 |
| DC Orange 4 | 0.20 |
| Acid red 33 | 0.20 |
| Benzyloxyethanol | 1.00 |
| Ethanol | 10.00 |
| Benzyl carbamate | 1.70 |
| Hydroxyethylcellulose | 1.50 |
| Sodium hydroxide | 0.25 |
| Phosphoric acid to pH 2.5 | q.s. |
| Dimethicone copolyol | 1.00 |
| Water | to 100 |

The viscosity of the compositions is 20,000 mPa.s measured at 20° C. with a Brookfield rotation viscosimeter, with spindle 5 at 5 rpm.

An intensive blue-black colour is achieved on goat tress. Exclusion of benzyl carbamate results in a less intensive colouration.

EXAMPLE 10

| Acid red 52 | 0.50 |
|---|---|
| DC Orange 4 | 0.25 |
| Benzyloxyethanol | 1.00 |
| Ethanol | 10.00 |
| Benzylurea | 1.00 |
| Benzyl carbamte | 0.70 |
| Hydroxyethylcellulose | 1.50 |
| Sodium hydroxide | 0.25 |
| Lactic acid | 4.00 |
| Phosphoric acid to pH 2.0 | q.s. |
| Dimethicone copolyol | 1.00 |
| Water | to 100 |

The viscosity of the compositions is 18,800 mPa.s measured at 20° C. with a Brookfield rotation viscosimeter, with spindle 5 at 5 rpm.

An intensive red colour is achieved on goat tress. Exclusion of benzyl carbamate and/or benzylurea results in a less intensive colouration.

EXAMPLE 11

|  | A | B |
|---|---|---|
| Acid red 33 | 0.5 | 0.5 |
| Ethanol | 15.00 | 15.00 |
| N-(2-methoxybenzyl) urea | 1.70 | — |
| PVM/MA Decadine Crosspolymer | 2.50 | 2.50 |
| Sodium hydroxide | 0.25 | 0.25 |
| Lactic acid | 4.50 | 4.50 |
| Dimethicone copolyol | 1.00 | 1.00 |
| Water | to 100 | to 100 |
| pH | 3.0 | 3.0 |

The viscosity of the compositions is 30,000 mPa.s measured at 20° C. with a Brookfield rotation viscosimeter, with spindle 5 at 5 rpm.

An intensive magenta colour is achieved on goat tress with composition A. With composition B the colour is less intensive

EXAMPLE 12

|  | A | B |
|---|---|---|
| Acid violet 43 | 0.3 | 0.3 |
| Ethanol | 15.00 | 15.00 |
| N-(2-methoxybenzyl) urea | 1.70 | — |
| PVM/MA Decadine Crosspolymer | 2.50 | 2.50 |
| Sodium hydroxide | 0.25 | 0.25 |
| Lactic acid | 4.50 | 4.50 |
| Dimethicone copolyol | 1.00 | 1.00 |
| Water | to 100 | to 100 |
| pH | 3.0 | 3.0 |

The viscosity of the compositions is 30,000 mpa.s measured at 20° C. with a Brookfield rotation viscosimeter, with spindle 5 at 5 rpm.

A dark violet colour is achieved on goat tress with composition A. With composition B the colour is less intensive For both examples 11 and 12, preparations A are examples to illustrate the invention. Preparations B are comparative preparations and not illustrating the invention Compositions are prepared as given under Examples 1 and 2. Colouring comparison is as well carried out in the same way as in Examples 1 and 2. The results are presented in Table III.

TABLE III

|  |  | Delta E |
|---|---|---|
| Example 11 | A (invention) | 70.3 |
|  | B (non-inventive) | 52.7 |
| Example 12 | A (invention) | 64.2 |
|  | B (non-inventive) | 44.7 |

It should be noted that the higher the delta E value the stronger the difference. It is very obvious from the results presented in Table III that the compositions comprising N-(2-methoxybenzyl) urea (compositions A) are showing higher colouring ability than those of without (compositions B).

Similar results are obtained with the examples below. Examples 13 to 15 are prepared in the same way as described for Examples 1 and 2 above.

EXAMPLE 13

| Acid Violet 43 | 0.30 |
|---|---|
| Acid black 1 | 0.30 |
| DC Orange 4 | 0.20 |
| Acid red 33 | 0.20 |
| Ethanol | 15.00 |
| N-(2-methoxybenzyl) urea | 1.70 |
| PVM/MA Decadine Crosspolymer | 2.50 |
| Sodium hydroxide | 0.25 |
| Lactic acid | 4.50 |
| Dimethicone copolyol | 1.00 |
| Water | to 100 |
| pH | 3.0 |

The viscosity of the compositions is 28,500 mPa.s measured at 20° C. with a Brookfield rotation viscosimeter, with spindle 5 at 5 rpm.

An intensive blue-black colour is achieved on goat tress. Exclusion of N-(2-methoxybenzyl) urea results in a less intensive colouration.

EXAMPLE 14

| Acid Violet 43 | 0.30 |
|---|---|
| Acid black 1 | 0.30 |
| DC Orange 4 | 0.20 |
| Acid red 33 | 0.20 |
| Benzyloxyethanol | 1.00 |
| Ethanol | 10.00 |
| N-(2-methoxybenzyl) urea | 1.00 |
| Benzylurea | 0.70 |
| Hydroxyethylcellulose | 1.50 |
| Sodium hydroxide | 0.25 |
| Phosphoric acid to pH 2.5 | q.s. |
| Dimethicone copolyol | 1.00 |
| Water | to 100 |

The viscosity of the compositions is 20,000 mPa.s measured at 20° C. with a Brookfield rotation viscosimeter, with spindle 5 at 5 rpm.

An intensive blue-black colour is achieved on goat tress. Exclusion of benzylurea and/or N-(2-methobenyl) urea results in a less intensive colouration.

EXAMPLE 15

| Acid red 52 | 0.50 |
|---|---|
| DC Orange 4 | 0.25 |
| Benzyloxyethanol | 1.00 |
| Ethanol | 10.00 |
| Benzyl carbamate | 0.70 |
| N-(2-methoxybenzyl) urea | 1.00 |
| Hydroxyethylcellulose | 1.50 |
| Sodium hydroxide | 0.25 |
| Lactic acid | 4.00 |
| Phosphoric acid to pH 2.0 | q.s. |
| Dimethicone copolyol | 1.00 |
| Water | to 100 |

The viscosity of the compositions is 18,800 mPa.s measured at 20° C. with a Brookfield rotation viscosimeter, with spindle 5 at 5 rpm.

An intensive red colour is achieved on goat tress. Exclusion of benzyl carbamate and/or N-(2-methoxybenzyl) urea results in a less intensive colouration.

The invention claimed is:

1. Colouring composition for hair, comprising benzyl carbamate and/or N-(2-methoxybenzyl) urea and at least one direct acting dyestuff.

2. Colouring composition for hair according to claim 1 wherein direct acting dyestuff are selected from acidic, anionic dyestuffs.

3. Colouring composition for hair according to claim 1, wherein it comprises benzyl carbamate and/or N-(2-methoxybenzyl) urea at a concentration of 0.1–10% by weight, calculated to the total composition.

4. Colouring composition for hair according to claim 1, wherein it comprises direct acting dyestuffs at a concentration of 0.001–5% by weight calculated to the total composition.

5. Colouring composition for hair according to claim 1, wherein it further comprises organic solvents.

6. Colouring composition for hair according to claim 1, wherein the pH of the composition is in the range from 1 to 5.

7. Colouring composition for hair according to claim 1, wherein it further comprises organic or inorganic acids or their mixtures.

8. Colouring composition for hair according to claim 1, wherein it further comprises at least one physiologically compatible hair conditioning agent selected from oily substances, non-ionic substances, cationic amphiphilic compounds, cationic polymers and their mixtures.

9. Colouring composition for hair according to claim 1, wherein it further comprises polymeric thickening agents.

10. Colouring composition for hair according to claim 1, wherein it has viscosity from 1,000 mPa.s to 60,000 mPa.s measured at 20° C. with Brookfield viscosimeter.

11. Colouring composition for hair, comprising benzyl carbamate and/or N-(2-methoxybenzyl) urea and at least one direct acting, acidic, anionic dyestuff.

12. Colouring composition for hair according to claim 11, wherein it comprises benzyl carbamate and/or N-(2-methoxybenzyl) urea at a concentration of 0.1–10% by weight, calculated to the total composition.

13. Colouring composition for hair according to claim 11, wherein it comprises direct acting dyestuffs at a concentration of 0.001–5% by weight calculated to the total composition.

14. Colouring composition for hair according to claim 11, wherein it further comprises organic solvents.

15. Colouring composition for hair according to claim 11, wherein the pH of the composition is in the range from 1 to 5.

16. Colouring composition for hair according to claim 11, wherein it further comprises organic or inorganic acids or their mixtures.

17. Colouring composition for hair according to claim 11, wherein it further comprises at least one physiologically compatible hair conditioning agent selected from oily substances, non-ionic substances, cationic amphiphilic compounds, cationic polymers and their mixtures.

18. Colouring composition for hair according to claim 11, wherein it further comprises polymeric thickening agents.

19. Colouring composition for hair according to claim 11, wherein it has viscosity from 1,000 mPa.s to 60,000 mPa.s measured at 20° C. with Brookfield viscosimeter.

* * * * *